United States Patent [19]

Proctor

[11] Patent Number: 5,470,876
[45] Date of Patent: Nov. 28, 1995

[54] TOPICAL SOD FOR TREATING HAIR LOSS

[76] Inventor: Peter H. Proctor, Twelve Oaks Medical Tower 4126 SW. Freeway, Suite 1616, Houston, Tex. 77027

[21] Appl. No.: 229,374

[22] Filed: Apr. 18, 1994

Related U.S. Application Data

[63] Continuation-in-part of Ser. No. 21,970, Feb. 24, 1993, Pat. No. 5,352,442, and a continuation-in-part of Ser. No. 193,228, Feb. 7, 1994, which is a continuation-in-part of Ser. No. 149,720, Jan. 29, 1988, abandoned, which is a continuation-in-part of Ser. No. 8,186, Jan. 28, 1987, abandoned, which is a continuation-in-part of Ser. No. 858,050, Apr. 30, 1986, abandoned, which is a continuation-in-part of Ser. No. 757,131, Jul. 18, 1985, abandoned.

[51] Int. Cl.$^6$ .......... A61K 31/28; A61K 38/00; C07F 1/08; C07F 3/06

[52] U.S. Cl. .......... 514/492; 514/6; 514/18; 514/19; 514/494; 514/499; 514/502; 556/148; 556/150; 556/132; 556/134; 556/135; 556/115; 556/116; 556/49; 556/50

[58] Field of Search .......... 514/492, 494, 514/499, 502, 6, 18, 19; 556/148, 150, 132, 134, 135, 115, 116, 49, 50

[56] References Cited

U.S. PATENT DOCUMENTS

| | | | |
|---|---|---|---|
| 2,409,754 | 10/1946 | Henze | 260/309.5 |
| 2,986,573 | 5/1961 | Topliss et al. | 167/65 |
| 3,257,390 | 6/1966 | Patchett | 260/239.55 |
| 3,461,461 | 8/1969 | Anthony et al. | 260/256.4 |
| 3,527,864 | 9/1970 | MacMillen et al. | 424/177 |
| 3,551,554 | 12/1970 | Herschler | 424/7.1 |
| 3,896,238 | 7/1975 | Smith | 424/358 |
| 4,139,619 | 2/1979 | Chidsey III | 424/45 |
| 4,184,039 | 1/1980 | Soldati et al. | 544/12 |
| 4,254,145 | 3/1981 | Birnbaum | 424/305 |
| 4,327,245 | 8/1982 | Shapiro | 424/214 |
| 4,344,941 | 8/1982 | Wiechert et al. | 424/243 |
| 4,367,227 | 1/1983 | Bingham | 424/243 |
| 4,444,762 | 4/1984 | Rajadhyaksha | 424/180 |
| 4,456,600 | 6/1984 | Wiechert et al. | 424/238 |
| 4,596,812 | 6/1986 | Chidsey III et al. | 424/251 |
| 4,665,054 | 5/1987 | Pickart | 514/18 |
| 4,760,051 | 7/1988 | Pickart | 514/6 |
| 4,866,067 | 9/1989 | Di Schiena | 514/275 |
| 4,877,770 | 10/1989 | Pickart | 514/18 |
| 5,120,831 | 6/1992 | Pickart | 530/331 |
| 5,177,061 | 1/1993 | Pickart | 514/18 |
| 5,214,032 | 5/1993 | Pickart | 514/16 |
| 5,252,559 | 10/1993 | Kronholm et al. | 514/18 |
| 5,256,678 | 10/1993 | Nakaguchi | 514/356 |

FOREIGN PATENT DOCUMENTS

| | | |
|---|---|---|
| 0249397 | of 0000 | European Pat. Off. |
| 0415598 | of 0000 | European Pat. Off. |
| 0027655 | 4/1981 | European Pat. Off. |
| 0273202 | 7/1988 | European Pat. Off. |
| 0327263 | 8/1989 | European Pat. Off. |
| 8022644 | of 0000 | Japan . |
| 2198132 | 6/1988 | United Kingdom . |
| 8302558 | 8/1983 | WIPO . |
| 8404922 | 12/1984 | WIPO . |
| 8600616 | 1/1986 | WIPO . |
| 8700427 | 1/1987 | WIPO . |

OTHER PUBLICATIONS

Myllyla et al., Biochemical and Biophysical Research Communications, vol. 89, No. 1, pp. 98–102 (1979).
Dooley et al., Biochemical and Biophysical Research Communications, vol. 96, No. 2, pp. 823–830 (1980).
Rao et al., Chemical Abstracts, vol. 80, No. 12, Abs. No. 64397u, p. 315 (1974).
Jahagirdar et al., Chemical Abstracts, vol. 82, No. 22, Abs. No. 145912b, p. 398 (1975).
Straehle et al., Chemical Abstracts, vol. 93, No. 3, Chem Abs. No. 21526m (1980).
Anderson, Chemical Abstracts, vol. 90, pp. 311K (1979).
Ando et al., Chemical Abstracts, 93:79872n (1980).
Bazzano et al., Journal of American Academy of Dermatology, vol. 15, pp. 880–883 (1986).
Berry, Pharmacology of the Skin, vol. 1, pp. 121–137 (1987).
Cheng et al., Archives of Dermatological Research, vol. 278, pp. 470–473 (1986).
Cumming et al., Journal of American Medical Association, vol. 247, pp. 1295–1298 (1982).
Current Therapy, pp. 599–603 (1984).
Dahl, Men's Fitness, pp. 93–95 (Feb. 1989).
Dawber, Dermatologica, vol. 175, suppl. 2, pp. 23–28 (1987).
DeVillez, Archives of Dermatology, vol. 121, pp. 197–202, (1985).
Dermatologica, vol. 175, suppl. 2, pp. 1–56 (Oct. 1987).
Dostert et al., Xenobiotica, vol. 15, No. 10, pp. 799–803 (1985).
Ehman et al., Investigative Radiology, vol. 21, pp. 125–131 (1986).
Feelisch et al., Evr. Journal of Pharmacology, vol. 139, pp. 19–30 (1987).
Feelisch et al., Evr. Journal of Pharmacology, vol. 142, pp. 405–409 (1987).
Fiedler, Dermatologica, vol. 175, suppl. 2, pp. 29–35 (1987).
Fox et al., Annals of the New York Academy of Sciences, vol. 411, pp. 14–19 (1983).
Goffman et al., International Journal of Radiation, Oncology, Biology and Physics, vol. 22, pp. 803–806 (Nov. 4, 1992).
Headington, Current Therapeutic Research, vol. 36, pp. 1098–1105 (1984).
Hearse et al., Circulation Research, vol. 60, pp. 375–383 (1987).

(List continued on next page.)

Primary Examiner—Porfirio Nazario-Gonzales
Attorney, Agent, or Firm—Sroufe, Payne & Lundeen

[57] ABSTRACT

SOD for treating hair loss is disclosed. The SOD has utility in a topical pharmaceutical formulation for the cosmetic treatment of hair loss and the cosmetic stimulation of hair growth. The SOD comprises copper salicylate, copper aspirinate, indomethacin-copper, or a complex of an amino acid or peptide and a transition metal.

19 Claims, No Drawings

OTHER PUBLICATIONS

Herschler, *Chemical Abstracts*, vol. 78, pp. 115–239 (1973).
Ignarro et al., *Biochemia et. Biophysica Acta*, vol. 631, pp. 221–231 (1980).
*J. Soc. Cosmetology Chem.*, (Italy) vol. 33, pp. 95–96 (Mar./Apr. 1982).
*Journal of American Medical Association*, vol. 260, No. 20 (1988).
Karlsson et al., *Journal of Cyclic Nucleotide and Protein Res.*, vol. 10, No. 4, pp. 309–315 (1985).
Kvedar, *Journal of American Academic Dermatology*, vol. 12, pp. 215–225 (1985).
*Longevity*, vol. 2, No. 3, p. 26 (Jan. 1988).
Lucky, *Archives of Dermatology*, vol. 121, pp. 57–62 (1985).
Messina, *Current Therapeutic Research*, vol. 34, pp. 319–324 (1983).
Messina, *Current Therapeutic Research*, vol. 38, pp. 269–282 (1985).
Mitchell et al., IBC USA Conference, South Natick, Mass. (June. 27, 1991).
Mittal et al., *Proc. of National Academy of Science*, USA, vol. 74, No. 10, pp. 4360–4364 (1977).
Palmer et al., *Nature*, vol. 327, pp. 524–526 (Jun. 11, 1987).
Parrett et al., *Journal of Pharmacology*, vol. 91, pp. 49–59 (1987).
*Physician's Desk Reference*, pp. 883, 977–978, 1782–1785, 1961 (1983).
Proctor et al., *Physiological Chemistry and Physics in Medical NMR*, vol. 16, pp. 175–195 (1984).
Ross, U.S. Department of Commerce, National Bureau of Standards, *Publication NSRDS–NBS59* (Jan. 1977).
Sekura, *Advances of Biology and Skin*, vol. XII, pp. 257–269, (1972).
Shapiro et al., *Journal of Clinical Endocrinology and Metabolism*, vol. 51, pp. 429–430 (1980).
Stewart, *International Journal of Dermatology*, vol. 17, pp. 167–179 (1978).
Thompson, *Federal Drug Administration Consumer*, pp. 10 and 12 (Mar. 10, 1981).
Tiffany–Castiglion, *Biochemical Pharmacology*, vol. 31, No. 2, pp. 181–188 (1982).
Torre (Ed). *Annals of the New York Academy of Sciences*, vol. 411, Table of Contents (1983).
Vermorken, *Acta Dermatovener* (Stockholm), vol. 63, pp. 268–269 (1982).
Voorhees (Ed.), *Dermatologica*, vol. 175, suppl. 2, pp. 1–56 (1987).
Watanabe et al., *Archives of Dermatological Research*, vol. 278, pp. 470–473 (1986).
Weissmann, *Archives of Dermatology*, vol. 121, pp. 57–62 (1985).
Yoshioka et al. *(Archives of Dermatological Research*, vol. 278, pp. 177–183 (1986).
Proctor, *Archives of Dermatology*, p. 1146 (Aug. 1989).

TOPICAL SOD FOR TREATING HAIR LOSS

CROSS-REFERENCE TO RELATED APPLICATIONS

This application is a continuation-in-part of applications 08/021,970, filed Feb. 24, 1993 now U.S. Pat. No. 5,352,442 and 08/193,228, filed Feb. 7, 1994 now allowed, which are continuations-in-part of application 07/149,720, filed Jan. 29, 1988, abandoned; which is a continuation-in-part of application 07/008,186, filed Jan. 28, 1987, abandoned; which is a continuation-in-part of application 06/858,050, Apr. 30, 1986, abandoned; which is a continuation-in-part of application 06/757,131, Jul. 18, 1985, abandoned.

FIELD OF THE INVENTION

This invention relates to topical superoxide dismutase (SOD), and the treatment of hair loss herewith.

BACKGROUND OF THE INVENTION

Recently, several anti-alopecia agents such as minoxidil and cyoctol have gained attention. However, most of these anti-alopecia agents are only minimally effective in some cases and/or can cause adverse dermatological or systemic reactions. Minoxidil, for example, is a therapeutic antihypertensive. Thus, the search continues for new, safer and more effective anti-alopecia agents which can be used without the risk of undesirable antihypertensive effects.

SUMMARY OF THE INVENTION

Applicant has discovered that SOD can be used as a topical anti-alopecia agent which can desirably be essentially free of antihypertensives, for example, to stimulate cosmetic hair growth.

In one embodiment, the present invention provides a method for stimulating hair growth. The method comprises the step of applying to skin in a topical pharmaceutical carrier a transition metal compound having SOD activity. The SOD active compound is selected from one or more of copper salicylate, copper aspirinate, indomethacin-copper and a complex of an amino acid or peptide and a transition metal. The amino acid is selected from one or more of glycine, histidine, lysine, arginine, cysteine and methionine, and the metal is selected from one or more of copper, iron, zinc and manganese. The peptide consists of glycine, histidine, lysine, arginine, cysteine or methionine. The peptide is selected from one or more of histidyl lysine, glycyl histidine, glycyl hystidyl lysine and lysyl histidyl lysine.

In another embodiment, the present invention provides a composition suitable for treating hair loss. The composition comprises a transition metal compound having SOD activity formulated in a suitable topical pharmaceutical carrier. The SOD active compound is selected from copper salicylate, copper aspirinate, indomethacin-copper and a complex of an amino acid and a transition metal. The amino acid is selected from glycine, histidine, lysine, arginine, cysteine and methionine, and the metal is selected from copper, iron, zinc and manganese.

In a further embodiment, the present invention provides a composition useful for treating hair loss comprising a transition metal compound of the formula R-M having superoxide dismutase activity. R is a salicyl, acetylsalicyl or indomethacin group and M is copper, iron, zinc or manganese. The composition includes a topical pharmaceutical carrier.

DETAILED DESCRIPTION OF THE INVENTION

In the present invention, superoxide dismutase (SOD) is compounded in a topical formulation. The pharmaceutical carrier, in which the SOD is generally substantially homogeneously dispersed can be an aqueous dispersion or suspension, or a water-in-oil or oil-in-water emulsion. Pharmaceutical carriers which can be mentioned include water, urea, alcohols and glycols such as methanol, ethanol, propanol, butanol, ethylene glycol, propylene glycol, and the like.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

The SOD can be enzymatic or an enzyme mimic, such as, for example, metal complexes of amino acids, peptides and other organic acids. Complexes of zinc and the transition metals, typically copper, iron and manganese, are known to have SOD activity. Preferred amino acids and peptides include the amino acids glycine, histidine, lysine, arginine, cysteine, methionine, and the like, and peptides comprised predominantly thereof. Representative examples include copper salicylate, copper aspirinate and indomethacin-copper.

Effective amounts of the SOD generally range from about 0.01 to about 20% by weight of the topical composition, more preferably from about 0.1 to about 10% by weight, most preferably from about 0.5 to about 3% by weight, but more or less can be present in the composition depending on the particular SOD formulation and the treatment conditions. In general, topical applications to the scalp of SOD having about 300 units of activity per application, or more, are sufficient.

The topical SOD can be used alone or in combination with other hair growth stimulants or additaments, which are available to enhance hair growth stimulation, such as, for example, the hydroxyl radical scavengers, antiandrogens and others described in International Publication No. WO 87/00427 (International Application No. PCT/US86/01393) published on Jan. 29, 1987; and European Patent Application No. 89300785.6, Publication No. 0327263/A1, published Aug. 9, 1989; both of which are hereby incorporated in their entirety herein as though fully set forth verbatim, including reference therein to the publication of Ross & Ross, "Selected Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the topical SOD is applied to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topical SOD is not limited thereto, however, and the stimulation of hair growth can include an increased rate of growth, increased hair diameter, follicular neogenesis, and the like, as well as inhibiting hair loss or alopecia from progressing, for example, in male pattern baldness, or during the course of treatment with other therapeutic agents known to induce hair loss, such as chemotherapy or radiation therapy in cancer treatment. The topical SOD can, if desired, be essentially free of minoxidil and other antihypertensives for use by individuals sensitive to them. The invention is illustrated by way of the following examples:

EXAMPLE 1

A medicated shampoo was prepared by adding 500 mg of copper salicylate to a commercially available non-medicated shampoo, and allowing the mixture to dissolve for 2–3 days. The shampoo was then used in a normal manner 2–7 times per week, e.g. wetting the hair, working a small amount (5–20 ml) of the shampoo into the hair and scalp, and rinsing after 1–3 minutes of contact with the scalp. Stimulation of hair growth was observed in 2–4 months.

EXAMPLE 2

Copper salicylate was suspended in deionized water at 1 g/100 ml. The suspension was applied twice daily to thinning areas of the scalp at 8–10 drops per application. Stimulation of hair growth was observed in 2–4 months.

EXAMPLE 3

A formulation was prepared by mixing the following together:

TABLE 1

| Ingredient | Amount |
|---|---|
| Water | 1600 ml |
| Spironolactone | 100 g |
| Copper Salicylate | 50 g |
| BHT | 50 g |
| Ascorbyl Palmitate | 50 g |
| Minoxidil | 1.2 g |
| Phenytoin | 50 g |
| Tretinoin | 2 g |
| Arginine | 50 g |

The mixture was then blended together with 900 ml of dimethylsulfoxide and 4.08 kg of Dermovan cream vehicle to make a lotion. Daily topical application gives better hair growth stimulation than compared to any component alone.

EXAMPLE 4

A lotion is made by homogenizing the following ingredients in the proportions indicated in Table 2:

TABLE 2

| INGREDIENT | PROPORTION |
|---|---|
| Copper aspirinate | 0.1 g |
| Ascorbyl palmitate | 0.5 g |
| Dermovan emulsion | 100 g |

The preparation is applied at a rate of about 0.5–1 ml one to three times per day to the affected area until hair growth is stimulated in about three months.

EXAMPLE 5

Another lotion is made by homogenizing the following proportions of ingredients:

TABLE 3

| INGREDIENT | PROPORTION |
|---|---|
| Lysyl-histidyl-lysine | 50 mg |
| Cupric chloride | 50 mg |
| Spironolactone | 0.5 g |
| Water | 30 ml |
| Propylene glycol | 30 ml |
| Ethanol | 20 ml |

The preparation is applied at a rate of about 0.5–1 ml one to three times per day to the affected area until hair growth is stimulated in about three months.

EXAMPLE 6

To demonstrate of hair stimulating activity of the peptide-metal complex of the present invention, a peptide-metal complex is used in a lotion. The peptide comprises glycyl-(L)-histdyl-(L)-lysyl-(L)-valyl-(L)-phenylalanyl-(L)-valine and the metal comprises copper (II). The ratio of peptide to metal ion in the complex is 2:1. The ingredients are homogenized into a topical lotion in the proportions stated in Table 4. Lotion is then applied to mice which have been shaved. Hair growth at the treated site is considered a positive response.

TABLE 4

| INGREDIENT | PROPORTION |
|---|---|
| peptide:Cu complex | 1% (wt/wt) |
| Nonoxynol-9 | 5% |
| Unibase cream | 94% |

Four of the five mice (80%) treated with the topical composition show accelerated hair growth ill the area of topical application. Similar results are reported in Pickart U.S. Pat. No. 5,120,831 which is hereby incorporated herein by reference.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

I claim:

1. A method for stimulating hair growth comprising the step of:
    applying in a topical pharmaceutical carrier to skin a transition metal compound having SOD activity, said compound selected from copper salicylate, copper aspirinate, indomethacin-copper and a complex of an amino acid or peptide and a transition metal, wherein the peptide consists of amino acids selected from glycine, histidine, lysine, arginine, cysteine or methionine.

2. The method of claim 1, wherein the amino acid of the amino acid-metal complex is selected from glycine, histidine, lysine, arginine, cysteine and methionine, and the metal is selected from copper, iron, zinc and manganese.

3. The method of claim 1, wherein the peptide is selected from histidyl lysine, glycyl histidine, glycyl hystidyl lysine and lysyl histidyl lysine.

4. The method of claim 1, wherein the transition metal compound is copper salicylate.

5. The method of claim 1, wherein the transition metal compound is copper aspirinate.

6. The method of claim 1, wherein the transition metal compound is indomethacin-copper.

7. a composition suitable for treating hair loss, comprising:

- a transition metal compound having SOD activity selected from copper salicylate, copper aspirinate, indomethacin-copper, and a complex of a basic amino acid and a transition metal; and
- a topical pharmaceutical carrier selected from oil and water emulsions, urea, propanol, butanol and glycols.

8. The composition of claim 7, wherein the amino acid is selected from glycine, histidine, lysine, arginine, cysteine and methionine, and the metal is selected from copper, iron, zinc and manganese.

9. The composition of claim 7, wherein the transition metal compound is copper salicylate.

10. The composition of claim 7, wherein the transition metal compound is copper aspirinate.

11. The composition of claim 7, wherein the transition metal compound is indomethacin-copper.

12. A composition useful for treating hair loss, comprising:

- a transition metal compound of the formula R-M having superoxide dismutase activity wherein R is salicyl, acetylsalicyl or indomethacin, and M is copper, iron, zinc, or manganese; and
- a topical pharmaceutical carrier selected from creams, lotions, shampoos and cream rinses.

13. The composition of claim 12, wherein R is salicyl.

14. The composition of claim 12, wherein R is acetylsalicyl.

15. The composition of claim 12, wherein R is indomethacin.

16. The composition of claim 12, wherein M is copper.

17. The composition of claim 12, wherein M is iron.

18. The composition of claim 12, wherein M is zinc.

19. The composition of claim 12, wherein M is manganese.

* * * * *

UNITED STATES PATENT AND TRADEMARK OFFICE
CERTIFICATE OF CORRECTION

PATENT NO. : 5,470,876
DATED : November 28, 1995
INVENTOR(S) : Peter H. Proctor

It is certified that error appears in the above-indentified patent and that said Letters Patent is hereby corrected as shown below:

In column 1, line 46, insert --preferably-- before "selected".

In column 1, line 49, insert --preferably-- before "selected".

In column 1, line 57, insert -- preferably-- before "selected".

In column 1, line 59, insert --preferably-- before "selected".

In column 2, line 46, delete the comma after "additaments".

In column 4, line 40, delete "ill" and replace it with --in--.

In column 5, line 8, capitalize the first word "a".

Signed and Sealed this

Ninth Day of April, 1996

Attest:

Attesting Officer

BRUCE LEHMAN

Commissioner of Patents and Trademarks